(12) United States Patent
Grummt et al.

(10) Patent No.: US 6,713,293 B1
(45) Date of Patent: Mar. 30, 2004

(54) ENCAPSULATED CELLS CONTAINING AN AMPLIFIED EXPRESSION VECTOR AS A DRUG DELIVERY DEVICE

(76) Inventors: Friedrich Grummt, Walther-von-der-Vogelweide Strasse 55, Würzburg (DE), 97074; Birgitta Sauer, Meichelbeek Strasse 2, Penzberg (DE), 82377; Martha Müller, Ursulinengasse 15, Würzburg (DE), 97070

(*) Notice: Subject to any disclaimer, the term of this patent is extended or adjusted under 35 U.S.C. 154(b) by 0 days.

(21) Appl. No.: 09/246,309

(22) Filed: Feb. 8, 1999

(51) Int. Cl.$^7$ .............................................. C12N 11/10
(52) U.S. Cl. ........................ 435/182; 435/325; 435/382
(58) Field of Search .......................... 424/93.21, 422, 424/451; 435/325, 382, 182

(56) References Cited

U.S. PATENT DOCUMENTS

| | | | |
|---|---|---|---|
| 4,442,203 A | 4/1984 | Varshavsky | 435/6 |
| 5,283,187 A | 2/1994 | Aebischer et al. | 435/182 |
| 5,300,436 A | * 4/1994 | Goldstein et al. | 435/252.3 |
| 5,550,050 A | 8/1996 | Holland et al. | 435/382 |
| 5,639,275 A | 6/1997 | Baetge et al. | 604/891.1 |
| 5,650,148 A | 7/1997 | Gage et al. | 424/93.2 |
| 5,653,975 A | 8/1997 | Baetge et al. | 424/93.1 |
| 5,656,481 A | 8/1997 | Baetge et al. | 435/325 |
| 5,676,943 A | * 10/1997 | Baetge et al. | 435/93.21 |
| 5,704,910 A | * 1/1998 | Humes | 604/52 |
| 5,750,103 A | 5/1998 | Cherksey | 424/93.21 |
| 5,756,455 A | 5/1998 | Kinzler et al. | 514/12 |
| 5,762,959 A | 6/1998 | Soon-Shiong et al. | 424/451 |
| 5,795,790 A | 8/1998 | Schinstine et al. | 435/382 |
| 5,798,113 A | 8/1998 | Dionne et al. | 424/422 |
| 5,800,828 A | 9/1998 | Dionne et al. | 424/422 |
| 5,800,829 A | 9/1998 | Dionne et al. | 424/422 |
| 5,833,979 A | 11/1998 | Schinstine et al. | 424/93.21 |
| 5,834,001 A | 11/1998 | Dionne et al. | 424/422 |
| 5,837,234 A | 11/1998 | Gentile et al. | 424/93.7 |
| 5,840,576 A | 11/1998 | Schinstine et al. | 435/325 |
| 5,842,431 A | 12/1998 | Wu | 424/93.21 |
| 5,853,385 A | 12/1998 | Emerich et al. | 604/500 |
| 5,853,717 A | 12/1998 | Schinstine et al. | 424/93.21 |
| 5,861,290 A | 1/1999 | Goldsmith et al. | 435/172.3 |

FOREIGN PATENT DOCUMENTS

| | | | | |
|---|---|---|---|---|
| DE | 4324671 A | * 5/1994 | | C12N/15/69 |
| WO | WO 94/10302 A1 | * 10/1993 | | |

OTHER PUBLICATIONS

Winn, S.R. et al., Polymer–encapsulated cells . . . , Proceedings of the National Academy of Science, V91, p2324–2328, Mar. 1994.*
Bendig. 1988. The production of foreign proteins in mammalian cells. in Genetic Engineering vol 7, pp. 91–127.*
Wegner et al. 1989. Nucleic Acids Research 17:9909–9932.*
Aebischer et al., 1991, "Long–Term Cross–Species Brain Transplantation of a Polymer–Encapsulated Dopamine–Secreting Cell Line", *Experimental Neurology* 111:269–275.
Aebischer et al., 1994, "Functional Recovery in Hemiparkinsonian Primates Transplanted with Polymer–Encapsulated PC12 Cells", *Experimental Neurology* 126:151–158.
Bogdahn et al., 1989, "Autocrine Tumor Cell Growth–inhibiting Activities from Human Malignant Melanoma", *Cancer Research* 49:5358–5363.
Freed et al., 1992, "Survival of Implanted Fetal Dopamine Cells and Neurologic Improvement 12 to 46 Months After Transplantation for Parkinson's Disease", *New England Journal of Medicine* 327:1549–1555.
Goetz et al., 1989, "Multicenter Study of Autologous Adrenal Medullary Transplantation to the Corpus Striatum in Patients with Advanced Parkinson's Disease", *N. Eng. J. Med.* 320:337–341.
Hemann et al., 1994, "High–Copy Expression Vector Based on Amplification–Promoting Sequences", *DNA and Cell Biology* 13:437–445.
Lindvall et al., 1990, "Grafts of Fetal Dopamine Neurons Surive and Improve Motor Function in Parkinson's Disease", *Science* 237:574–577.
Spencer et al., 1992, "Unilateral Transplantation of Human Fetal Mesencephalic Tissue Into The Caudate Nucleus Of Patients with Parkinson's Disease", *New England Journal of Medicine* 327: 1541–1548.
Tresco et al., 1992, "Polymer–encapsulated PC12 Cells: Long–Term Survival and Associated Reduction in Lesion–Induced Rotational Behavior", *Cell Transplantation* 1:255–264.
Wegner et al., 1989, "Cis–acting suquences from mouse rDNA promote plasmid DNA amplification and persistence in mouse cells: implication of HMG–I in their function", *Nucleic Acids Research* 17:9909–9932.
Winn et al., 1991, "Behavioral Recovery following Intrastriatal Implantation of Microencapsulated PC12 Cells", *Ecperimental Neurology* 113:322–329.

* cited by examiner

*Primary Examiner*—James Ketter
(74) *Attorney, Agent, or Firm*—Dorsey & Whitney LLP; Birgit Millauer

(57) ABSTRACT

The present invention provides a drug delivery device comprising encapsulated cells that contain multiple copies of an expression cassette. The drug delivery device of the present invention is useful to supply an animal, including a human, with a therapeutically desirable molecule, including physiological activities lacking in disease conditions or antagonist against conditions in an animal, especially a human.

21 Claims, 5 Drawing Sheets

Figure 1:
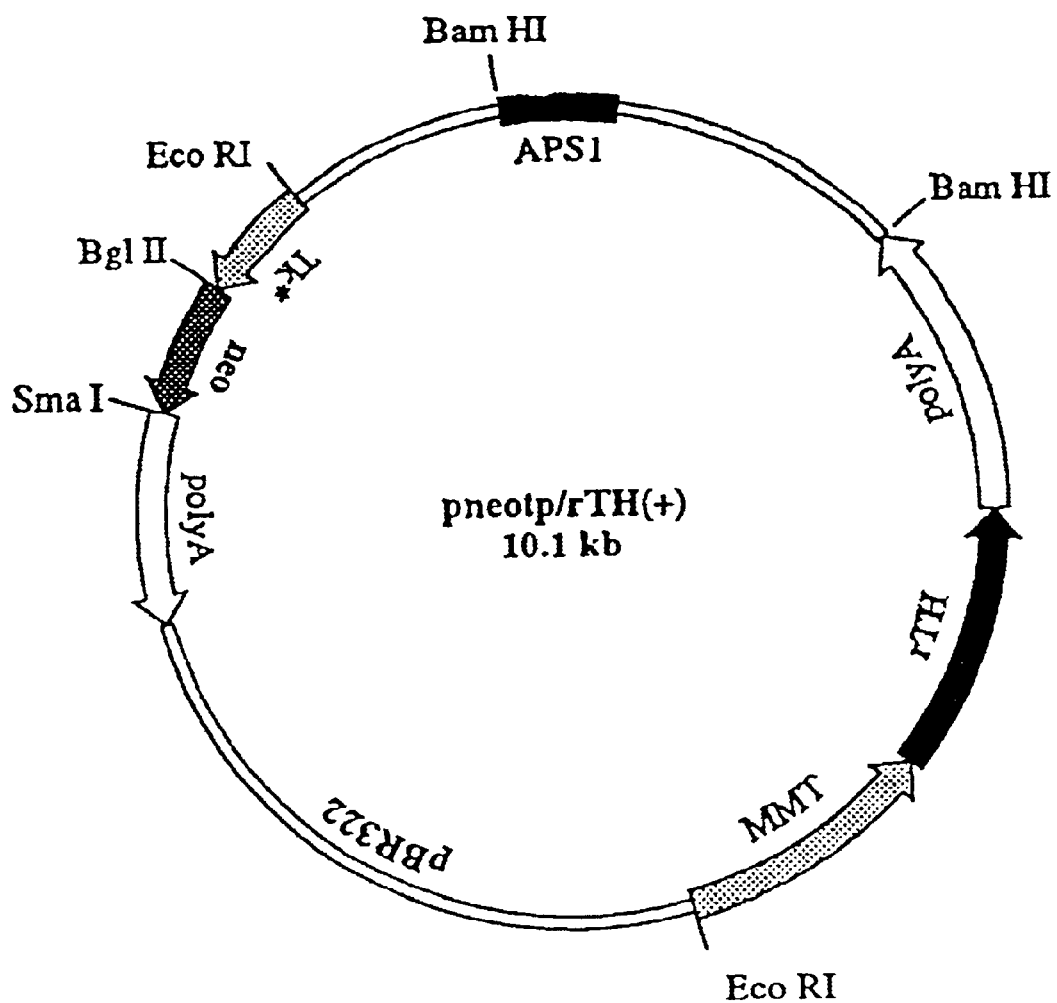

(4 of 5 Drawing Sheet(s) Filed in Color)

ENCAPSULATED CELLS CONTAINING AN AMPLIFIED EXPRESSION VECTOR AS A DRUG DELIVERY DEVICE

1. FIELD OF THE INVENTION

The present invention relates to a drug delivery device comprising eukaryotic cells that contain an amplified expression vector. The drug delivery device of the invention is designed to provide physiological activities lacking in disease conditions or antagonists against conditions in an animal, especially a human.

2. BACKGROUND OF THE INVENTION

The ability of eukaryotic cells to synthesize molecules results from a variety of metabolic activities which are provided by a variety of cellular factors, for example growth factors, hormones and enzymes. These metabolic activities are often part of metabolic pathways and aberrant control or a partial or complete lack of such an activity in an animal may be responsible for a disease condition in that animal, for example a human. Such metabolic activities may relate to energy metabolism, structural metabolism, signal transduction, or any kind of biochemical activity.

Attempts to restore or inhibit a metabolic activity to a diseased animal, including a human, have been made through gene therapy, i.e., through introduction of foreign polynucleotide sequences encoding agonists or antagonists into the genome of a cell in an animal. When gene therapy is carried out directly on an animal, it is difficult to control the outcome of the introduction of such sequences. For example, the foreign polynucleotide sequences may disrupt a cellular gene and thus lead to serious pathological conditions (e.g., cancer). Another problem often encountered in gene therapy is that the foreign polynucleotide sequences do not remain stably integrated and expressed in the target cells.

Gene therapy can be rendered much more controlled and effective if it is carried out in cultured cells which are then transferred into the diseased animal. However, in order to avoid the rejection of the manipulated cells that are transferred into an animal by its immune system, it is necessary to use autologous cells, derived from the treated animal itself. Alternatively, the manipulated cells may be from a different animal as the diseased animal (and possibly from a different species), thus requiring efforts to prevent rejection of the transferred cells through the immune system of the recipient animal.

One approach to prevent the rejection of foreign cells in an animal is to encapsulate such cells. By incorporating the cells into a protective shell, i.e., capsule, which prevents the immune system of the recipient animal to reach the cells, the cells can survive and remain metabolically active in the recipient animal. Critical to such survival is the fact that the capsule allows the passage of small molecules in and out of the capsule, thus providing the encapsulated cells with access to nutrients and the recipient animal to metabolic products of the encapsulated cells. As one or more of these metabolic products of the encapsulated cells is lacking in the recipient animal, the encapsulated cells effectively act as a drug pump.

A limitation when using such an encapsulation approach is that the capsules can take up only a limited number of cells and that not all cells within a capsule will survive over extended periods of time. In order to supply an effective level of the desired metabolic activity to the recipient animal, it is necessary to express such metabolic activity at a high level over extended periods of time in the encapsulated cells. A need exists for ways to make drug delivery through encapsulated cells more potent. The present invention provides such technology.

3. SUMMARY OF THE INVENTION

The present invention provides a drug delivery device ("device") and methods of making and using such a device. The device of the present invention is useful for many disease control and therapeutic strategies by taking advantage of the ability of a cell to provide pharmaceutically useful functions, for example the metabolism of a drug precursor. Thus, the device of the invention can, once transferred into a diseased animal, provide long term disease control.

In one embodiment, the device of the present invention comprises a eukaryotic cell that contains an exogenous polynucleotide ("exogenous polynucleotide") sequence, preferably in multiple copies, and that is located in a capsule. In one aspect, the exogenous polynucleotide comprises an amplification-promoting sequence and an expression cassette. In another aspect, the exogenous polynucleotide also comprises a selectable marker.

In one embodiment, an amplification-promoting sequence ("APS") useful for the exogenous polynucleotide in a device of the present invention, is capable of amplifying the number of copies of the exogenous polynucleotide in a eukaryotic cell. In a preferred aspect, an APS presented in SEQ ID NO:1 or SEQ ID NO:2 is used. In a further aspect, any polynucleotide that is substantially homologous to SEQ ID NOS:1 or 2 is also a useful APS in the exogenous polynucleotide. In another aspect, more than one APS is included in the exogenous polynucleotide, for example SEQ ID NOS:1 and 2. In a further aspect, one or more APSs are included in the exogenous polynucleotides, of which one or more is substantially homologous to either SEQ ID NOS:1 or 2 and of which one or more is identical to SEQ ID NOS:1 or 2.

An expression cassette useful in the exogenous polypeptide, in one embodiment, comprises a polynucleotide sequence that encodes a function of interest ("coding sequence") and a regulatory sequence. The coding sequence in the expression cassette, in one aspect, may encode a peptide, a polypeptide, a protein, a polynucleotide. In another aspect, the expression cassette may be specific for a polynucleotide or an oligonucleotide with a catalytic or an inhibitory activity. Preferably, the coding sequence is specific for a molecule that has a pharmacologically desirable activity or property. In another aspect, the coding sequence encodes a protein or a polypeptide with an enzyme activity that is lacking in a disease condition, for example an enzyme activity involved in the synthesis of a signal transduction molecule (e.g., a second messenger, serotonin, dopamin). In another aspect, the coding sequence is specific for a peptide, a polypeptide or a protein capable of regulating cell proliferation, cell differentiation, programmed cell death, signal transduction, gene expression, gene transcription, translation, etc. In another aspect the coding sequence is specific for aft antibody, an antibody fragment, an agonist of a naturally occurring molecule, an antagonist of a naturally occurring molecule, a neurotrophic factor, a neurotropic factor, a peptide hormone (e.g., a neurohormone), etc.

In another preferred embodiment, the coding sequence is specific for tyrosine hydroxylase, tryptophan hydroxylase, melanoma inhibitory activity, an insulin, an insulin precursor polypeptide, an enkephalin, an enkephalin precursor polypeptide, parathyroid hormone, a parathyroid hormone precursor polypeptide, enkephalinase, a neurotrophic factor, a neurotropic factor, or a homolog, orthologue, paralogue, analogue, or derivative of any of these, or a fusion polypeptide or protein that contains any of the above and a heterologous protein, polypeptide or peptide.

Preferably, the expression cassette contains a regulatory sequence. In one aspect, the expression cassette contains a promoter sequence and a polyadenylation sequence ("polyA sequence"). Promoter sequences useful for the expression cassette, in a preferred aspect, are active, i.e., capable of initiating gene transcription, in the cell type used in the device of the present invention. Useful promoters are active at least at a moderate level (i.e., a moderately strong promoter), preferably they are active at a high level (i.e., strong promoter). A constitutive and an inducible promoter may be used in the expression cassette, provided the promoter is sufficiently active. In another aspect, any polyA sequence that is sufficiently strong to induce polyadenylation of the transcripts of the expression cassette can be used.

In another aspect, the expression cassette may include an enhancer, an intron, a 5' and/or 3' untranslated region, an RNA stability regulating sequence or a combination of more than one of these elements.

In one embodiment, a eukaryotic cell is used in the device of the present invention. The cell preferably is capable of dividing multiple times, for example about 10 to about 300 times, or more than 300 times. In one aspect, the cell is transformed. In another aspect, the cell is derived from the same species as the species in which the device of the present invention is used.

In one embodiment, the cell containing the exogenous polynucleotide is encapsulated. In a preferred aspect, the capsule that contains the cell is double layered. In a preferred aspect, the cells of the device of the present invention are located in the inner layer. In another aspect, the capsule has more than two layers.

4. BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

FIG. 1. The TH expression plasmid prTH is shown. Based on the vector pBR 322 the TH expression vector contains three essential elements, (i) the TH expression cassette under control of the constitutive mouse metallothionein promoter (MMT), (ii) the selection cassette under control of a truncated thymidine kinase promoter (Tk*) and (iii) muAPS1 as an amplification-promoting sequence to obtain high-copy-number cells. Restriction sites essential for cloning are indicated.

Figure 2A:
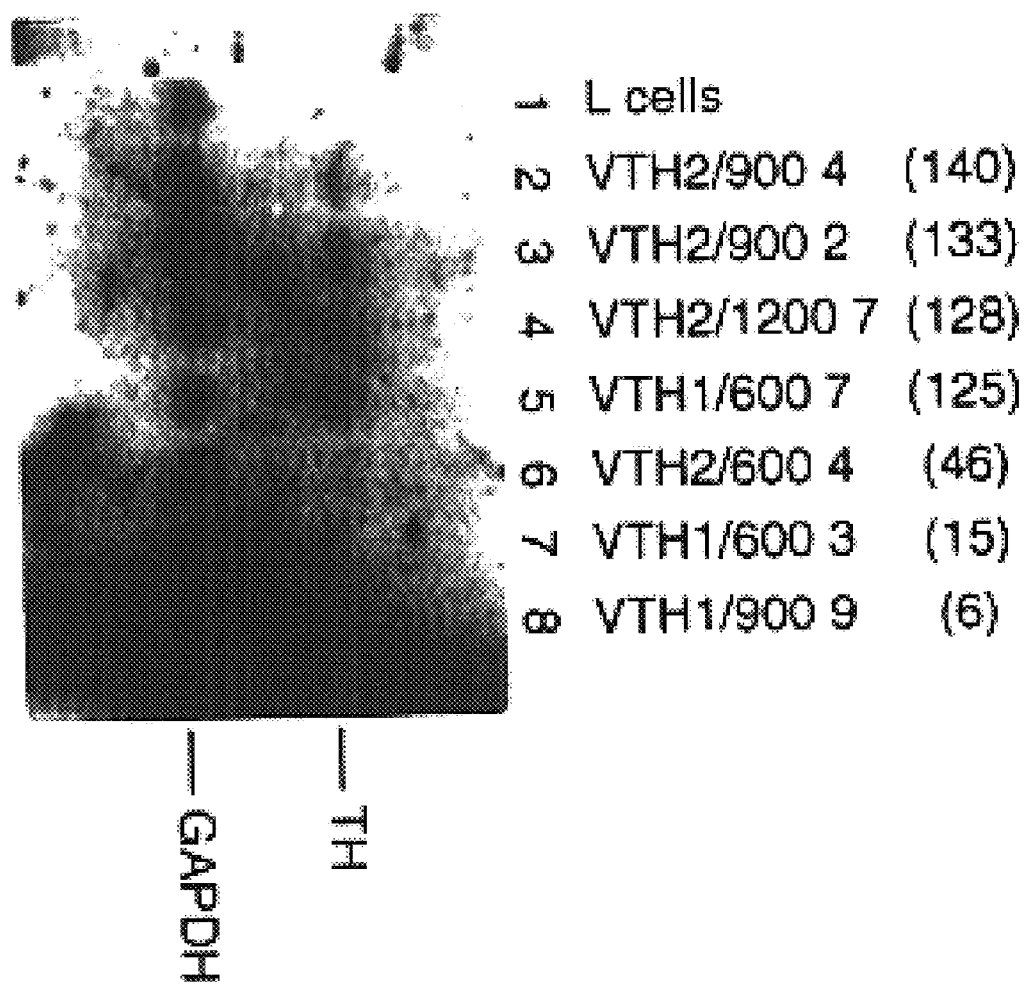
Figure 2B:
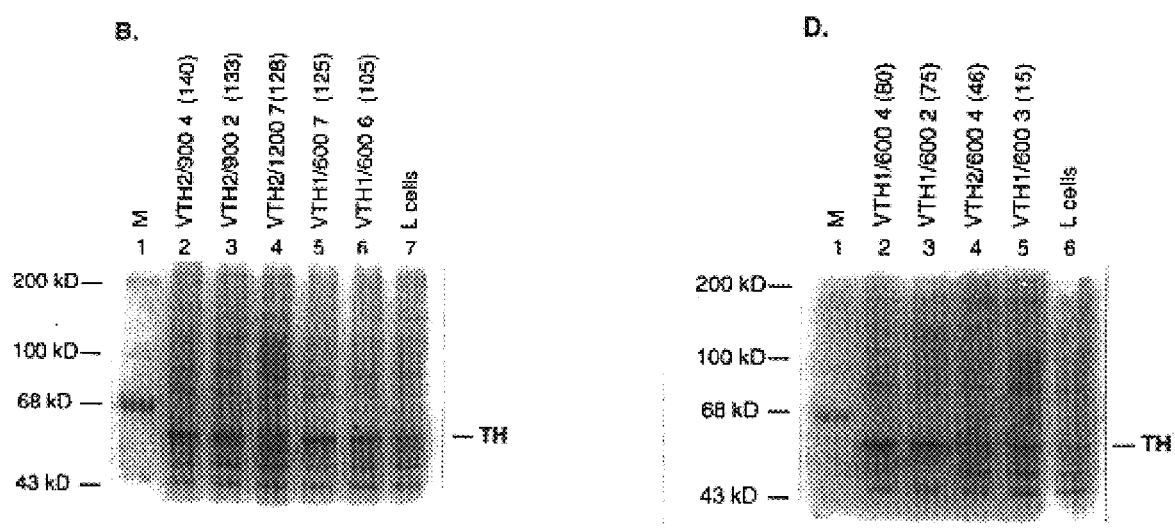

FIGS. 2A and 2B. Expression levels of TH mRNA and protein in various cell clones bearing different numbers of the TH cassette (in parenthesis) grown under different concentrations of G418 (600, 900 or 1,200 μg/ml). (A) Northern blot indicating the abundance of TH mRNA transcripts positively correlated with gene dosage. Internal control: GAPDH mRNA. (B) Western blot demonstrating the presence of high levels of TH protein in transformed L cells. (M is a protein standard.)

Figure 3:

FIG. 3. In situ hybridization of metaphase chromosomes from mouse L fibroblasts transformed by Px. Panel (a) and (c) show representative metaphase chromosome spreads, Panel (b) and (d) the same spreads at high magnification. In each metaphase spread a single HSR is visible.

Figure 4:
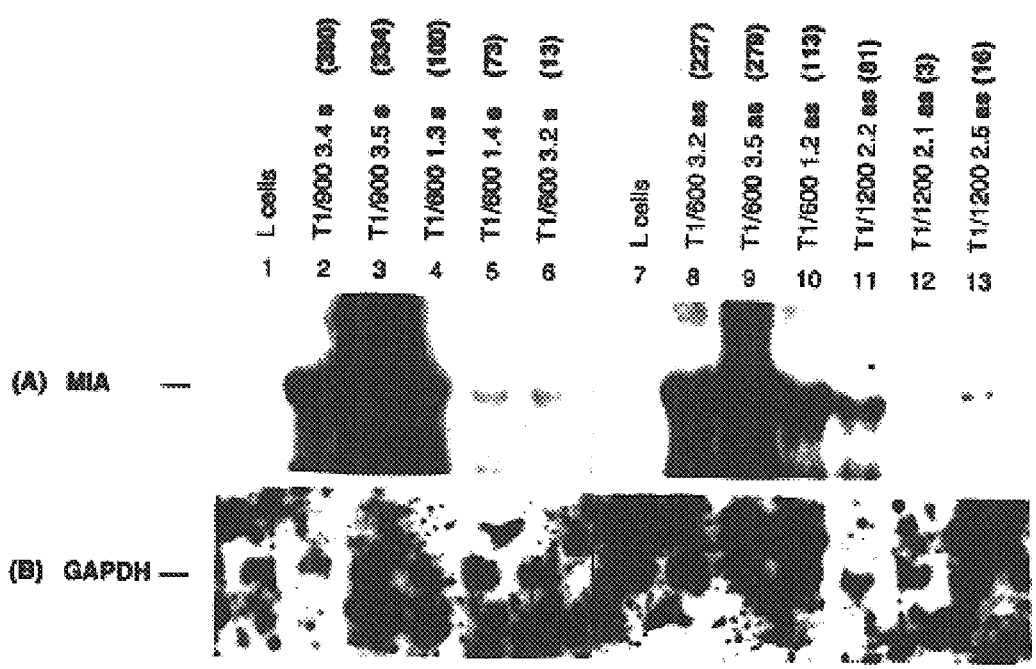

FIG. 4. Expression levels of MIA mRNA in various cell clones bearing different numbers of the MIA cassette (in parenthesis) grown under different concentrations of G418 (600, 900 or 1,200 μ/ml). The expression data on the Northern blot indicate that the abundance of MIA mRNA transcripts positively correlated with gene dosage. Internal control: GAPDH mRNA.

5. DETAILED DESCRIPTION OF THE INVENTION

5.1. Overview

The present invention relates to drug delivery devices that take advantage of the ability of most eukaryotic cells to synthesize or aid in the synthesis of molecules. The lack of one or more of these molecules is often responsible for a disease condition in an animal, for example a human. Thus, when properly supplied as drugs to a diseased animal, these molecules are useful in controlling and/or treating many disease conditions.

In one embodiment, the present invention provides drug delivery devices that are capable of synthesizing a molecule, for example a molecule having a pharmacological activity. When the device is transferred into an animal, the molecule is provided to that animal by the device of the present invention, i.e., the device acts as a drug pump which produces or aids in producing a drug.

The device of the present invention comprises encapsulated eukaryotic cells which contain an exogenous polynucleotide (i.e., exogenous to the cells). The exogenous polynucleotide contains an expression cassette that includes a coding sequence specific for a metabolic activity, for example an enzyme activity that is lacking in a disease condition. See, e.g., U.S. Pat. No. 5,082,670, which provides examples of such metabolic activities. The expression cassette further contains a promoter and a polyA sequence to regulate the proper transcription of the coding sequence. The exogenous polynucleotide can be constructed with any technique known in the art of molecular biology. For general background on molecular biology techniques, see, e.g., Ausubel F. M. et al., eds., 1989, Current Protocols in Molecular Biology, Green Publishing Associates, Inc., and John Wiley & sons, Inc., New York; Maniatis et al., 1989, Molecular Cloning A Laboratory Manual, Cold Spring Harbor Laboratory, New York; and U.S. Pat. No. 5,650,148.

The exogenous polynucleotide also contains an APS capable of amplifying the copy number of the exogenous polynucleotide in the genome of eukaryotic cells. Thus, the cells of the device of the present invention contain multiple copies of an expression cassette specific for a metabolic activity. As demonstrated in the Examples below, the expression of the coding sequence of the exogenous polynucleotide increases with an increase in the number of copies of the exogenous polynucleotide in the cells, i.e., gene dosage effect. This increased expression provides the metabolic activity supplied in the device of the present invention at a higher level and therefore makes the device a more potent drug pump than without amplification of the exogenous polynucleotide.

The exogenous polynucleotide used in the device of the present invention is up to about 50 kilobases ("kb") in size, preferably up to about 40 kb, more preferably up to about 30 kb and most preferably up to about 20 kb.

5.2. Amplification-Promoting Sequences

APSs useful for the device of the present invention are capable of amplifying (i.e., increasing) the number of copies of a polynucleotide sequence in a cell. For example, when an APS is integrated into an exogenous polynucleotide that is transfected into a proliferating cell, the number of copies of the exogenous polynucleotide will increase with increasing numbers of divisions of that cell. The exogenous polynucleotide will typically integrate into the genome of the cell following transfection. See, e.g., Hemann et al., 1994, DNA and Cell Biology 13:437–445; Meyer et al., 1993, Gene 129:263–268; Wegner et al., 1989, Nucleic Acids Research 17:9909–9932, which discuss APSs and their use.

The rate of amplification of the exogenous polynucleotide containing an APS useful for the device of the present invention can be expressed through the amplification factor, i.e., the number of copies of the exogenous polynucleotide found in a single host cell after 15 to 25 divisions of the host cell following transfection. An APS useful for the device of the present invention has an amplification factor of at least about 5, more preferably at least about 10, more preferably at least about 20, more preferably at least about 40, more preferably at least about 70, more preferably at least about 100 and most preferably at least about 150. See, e.g., U.S. Pat. Nos. 5,756,455 and 4,442,203, which discuss gene amplification and methods for its detection.

In one embodiment, one APS is included in the exogenous polynucleotide used in the device of the present invention. In another embodiment, more than one APS, for example two, are included in the exogenous polynucleotide.

In a preferred embodiment, an APS used in the device of the present invention has a sequence as presented in SEQ ID NO:1 or SEQ ID NO:2 (See, Wegner et al., 1989, Nucleic Acids Research 17:9909–9932) (Genbank accession numbers X52413 and X52412, respectively). In another preferred embodiment, an APS used in the device of the present invention has a sequence that is at least about 85% identical to a polynucleotide sequence as presented in SEQ ID NO:1 or SEQ ID NO:2, more preferably at least about 90%, more preferably at least about 95% and more preferably at least about 98%.

In another preferred embodiment, an APS useful for the device of the present invention is a polynucleotide that hybridizes under moderately stringent conditions to a polynucleotide that is complementary to SEQ ID NO:1 or SEQ ID NO:2. Moderately stringent hybridization conditions are well known in the art. For example, filters containing DNA are pretreated for 6 h at 55° C. in a solution containing 6×SSC, 5×Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 h at 55° C. The filters are then washed in approximately 1× wash mix (10× wash mix contains 3M NaCl, 0.6M Tris base, and 0.02M EDTA) twice for 5 minutes each at room temperature, then in 1× wash mix containing 1%SDS at 60° C. for about 30 min, and finally in 0.3× wash mix containing 0.1% SDS at 60° C. for about 30 min. The filters are then air dried and exposed to x-ray film for autoradiography.

In an alternative protocol, washing of filters is done twice for 30 minutes at 60° C. in a solution containing 1×SSC and 0.1% SDS. Filters are blotted dry and exposed for autoradiography.

Other conditions of moderate stringency which may be used are also well-known in the art, for example the washing of filters can be done at 37° C. for 1 h in a solution containing 2×SSC, 0.1% SDS. Another example of hybridization under moderately stringent conditions is washing in 0.2×SSC/0.1% SDS at 42° C. (Ausubel F. M. et al., eds., 1989, Current Protocols in Molecular Biology, Vol. I, Green Publishing Associates, Inc., and John Wiley & sons, Inc., New York).

In a more preferred embodiment, an APS useful for the device of the present invention is a polynucleotide that hybridizes under highly stringent conditions to a polynucleotide that is complementary to SEQ ID NO: 1 or SEQ ID NO:2. Hybridization under highly stringent conditions is well known in the art. For example, prehybridization of filters containing DNA to be screened is carried out for 8 h to overnight at 65° C. in a buffer containing 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. The filters are then washed in approximately 1× wash mix (10× wash mix contains 3M NaCl, 0.6M Tris base, and 0.02M EDTA) twice for 5 minutes each at room temperature, then in 1× wash mix containing 1% SDS at 60° C. for about 30 min, and finally in 0.3× wash mix containing 0.1% SDS at 60° C. for about 30 min. The filters are then air dried and exposed to x-ray film for autoradiography. In an alternative protocol, washing of filters is done for 37° C. for 1 h in a solution containing 2×SSC, 0.01% PVP, 0.01% Ficoll, and 0.01% BSA. This is followed by a wash in 0.1×SSC at 50° C. for 45 min before autoradiography. Another example of hybridization under highly stringent conditions is hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3).

5.3. Expression Cassettes

The exogenous polynucleotide used in the device of the present invention contains an expression cassette. The expression cassette contains a polynucleotide sequence specific for a metabolic activity, ie., coding sequence. The expression cassette further contains regulatory elements for the expression of the coding sequence, i.e., a promoter and a polyA sequence. Other regulatory elements that may be used in the expression cassette include an enhancer, an intron, 5' and/or 3' untranslated regions, RNA stability regulating sequences, etc.

5.3.1. Coding Sequences

The coding sequence is a polynucleotide sequence found in the exogenous polynucleotide of the present invention specific for a metabolic activity, i.e., any activity relevant to the biochemistry, physiology or pharmacology of the recipient animal. The coding sequence may encode a protein or a nucleotide factor.

The coding sequence in the expression cassette, in one aspect, encodes a peptide, a polypeptide, a protein, a polynucleotide or an oligonucleotide. Preferably, the coding sequence is specific for a molecule that has a pharmacologically desirable activity or property. In another aspect, the coding sequence encodes a protein or a polypeptide with an enzyme activity that is lacking in a disease condition, for example an enzyme activity involved in the synthesis of a signal transduction molecule (e.g., a second messenger, serotonin, dopamin). In another aspect, the coding sequence is specific for a peptide, a polypeptide or a protein capable of regulating cell proliferation, cell differentiation, programmed cell death, signal transduction, gene expression, gene transcription, translation, etc. In another aspect the coding sequence is specific for an antibody, an antibody fragment, an agonist of a naturally occurring molecule (e.g., an agonist of a receptor molecule in the recipient animal), an antagonist of a naturally occurring molecule (e.g., an antagonist of a receptor molecule in the recipient animal), a neurotrophic factor, a neurotropic factor, a peptide hormone (e.g., a neurohormone), etc.

In another aspect, the coding sequence may be specific for a non-naturally occurring molecule, e.g., protein, polypeptide, peptide, polynucleotide, oligonucleotide, etc. The device of the present invention is useful for the delivery of any molecule that can be provided through expression of a polynucleotide sequence in the expression cassette of the device and the molecule may be of any origin, whether natural or nonnatural. The purpose for expressing a particular polynucleotide sequence in the expression cassette of the device is of concern to the overall strategy pursued with the use of the device. However, the device itself is not limited in any way to particular classes of molecules that may be provided to the recipient animal through the device.

Proteins that may be encoded by the coding sequence include, but are not limited to, enzymes, precursor proteins and polypeptides of signal transduction peptides and polypeptides, growth factors, neurohormones, toxins, neurite promoting molecules, neurotropic factors and neurotrophic factors (e.g., brain derived neurotrophic factor, ciliary neurotrophic factor, nerve growth factors, etc.); enzymes involved in the synthesis of gangliosides, antibiotics, idenosin phosphates, cyclic adenosin monophosphate, cyclic guanosin monophosphate, nucleoside mono-, di- or triphosphates, steriods, glucosides, glycerides, catecholamines, endorphins, peptides, etc. See, e.g., U.S. Pat. Nos. 5,800,828; 5,798,113; 5,762,926; 5,656,481; 5,653,975; 5,650,148; 5,082,670, which discuss coding sequences and metabolic activities that can be expressed using the device of the present invention.

In another preferred embodiment, the coding sequence is specific for tyrosine hydroxylase, tryptophan hydroxylase, melanoma inhibitory activity, an insulin, an insulin precursor polypeptide, an enkephalin, an enkephalin precursor polypeptide, parathyroid hormone, a parathyroid hormone precursor polypeptide, enkephalinase, a neurotrophic factor, a neurotropic factor, or a homolog, orthologue, paralogue, analogue, or derivative of any of these, or a fusion polypeptide or protein that contains any of the above and a heterologous protein, polypeptide or peptide.

When choosing a coding sequence for the device of the present invention, it should be considered that the molecule of interest that is generated through expression of the coding sequence must be capable of leaving, e.g., diffusing out of, the capsule used in the device. For example, when the coding sequence is specific for a precursor to a peptide (e.g., a neurotransmitter, a peptide hormone, etc.), the permeability barrier of the capsule should be such that the peptide can leave the capsule, or such that the precursor can leave the capsule in case the precursor is not processed in the cells of the device of the present invention.

When the coding sequence is specific for an enzyme, the substrate of the enzyme should be available to that enzyme, for example through metabolic processing of precursors to the substrate molecule by other enzymes in the cell or through entry of the substrate into the cell. If an enzyme has more than one substrate, that substrate which yields the product of interest through catalysis of the enzyme should be available to the enzyme.

In case the coding sequence is specific for an enzyme that requires a co-factor, the co-factor should be available to the enzyme in the cells of the device of the present invention.

The coding sequence may be specific for a molecule designed to control, prevent or treat a disease, for example metabolic disorders, cancer, diabetes, neurodegenerative diseases, Alzheimer's, neuroregenerative diseases, heart disease, liver diseases, osteoporosis, obesity, arteriosclerosis, etc.

An example of peptides that can be produced using the device of the present invention are enkephalins. Enkephalins are neurohormone peptides that are synthesized in vivo as precursor polypeptides called preproenkephalin and proenkephalin which are processed to yield the enkephalin peptides (see, e.g., Kang et al., 1998, Brain Research 792:133–135; Liu et al., 1996, Journal of Neurochemistry 67:1457–1462). The processing of the preproenkephalin and proenkephalin polypeptide is carried out by peptidases, for example enkephalinase. See, e.g., U.S. Pat. Nos. 5,780,025 and 5,403,585, which describe enkephalinase and methods for its use.

The device of the present invention can be used, for example, to generate enkephalins. For example, one can use a cDNA specific for one or more of the enkephalin precursor peptides and polypeptides in the expression cassette. The enkephalin precursor is preferably expressed in a cell type that is capable of processing the precursor so that one or more mature enkephalin peptides are generated. Another way to generate enkephalins is to express a precursor polypeptide of enkephalins and processing enzymes required to make the individual enkephalin peptides. The particular enzymes needed to process the enkephalin precursors will depend on the cell type used in the device of the invention. Thus, the expression cassette, in this example, would contain more than one coding sequence, i.e., it would contain one coding sequence for the enkephalin precursor and at least one coding sequence for a processing enzyme. Typically, when an expression cassette contains more than one coding sequence, each coding sequence is under the control of its own regulatory elements to direct expression of each coding sequence. When used to express an enkephalin in the recipient animal, especially a human, the device of the invention is preferably located in the lumbar vertebrae.

As another example, the device of the present invention is useful for the generation of serotonin, i.e., 5-hydroxytryptophan. The rate limiting step in the synthesis of serotonin is the hydroxylation of tryptophan by the enzyme tryptophan hydroxylase (see, e.g., Wang et al., 1998, Journal of Neurochemistry 71:1769–1772; Tipper et al., 1994, Arch. Biochem. Biophys. 315:445–453; Kim et al., 1991, Brain Res. Mol. Brain Res. 9:277–283; Hanon et al., 1981, Journal of Physiology 77:269–279). Serotonin can be generated using the device of the present invention by incorporating a polynucleotide sequence specific for tryptophan hydroxylase into the expression cassette of the exogenous polynucleotide.

In another example, the device of the present invention is used to generate insulin. For example, a polynucleotide sequence specific for insulin or an insulin precursor can be used in the expression cassette of the device of the invention. See, e.g., U.S. Pat. Nos. 5,792,656 and 4,914,026, which discuss polynucleotides specific for insulin. The insulin specific polynucleotide may be operatively linked to a promoter that is responsive to induction by elevated concentrations of glucose. See, e.g., Marie et al., 1993, J. Biol. Chem. 268:23881–23890, which describes a glucose inducible promoter. The device of the invention, if designed with a glucose responsive promoter element and an insulin (or insulin precursor) specific polynucleotide, would be capable of generating insulin in the recipient animal when the glucose levels in that animal are elevated. Thus, the device would generate insulin in a glucose dependent manner, as is observed in the islets of Langerhans in the pancreas.

In another aspect, cells capable of increasing insulin production in response to elevated glucose concentration may be provided for the device of the present invention by using a coding sequence specific for a molecule that is part of the glucose sensing mechanism in cells. For example, one may use cells that are capable of expressing and processing insulin and introduce an exogenous polynucleotide into these cells that provides a glucose sensing activity, for example a glucose kinase gene or a glucose transporter gene. See, e.g., U.S. Pat. Nos. 5,792,656 and 5,747,325, which describe cells and polynucleotides useful for this aspect of the present invention.

A further example of using the device of the present invention is the expression of parathyroid hormone ("PTH"). PTH is a peptide hormone involved in the regulation of calcium metabolism. PTH is useful in controlling disease conditions, for example osteoporosis. PTH can further be used to regulate calcium homeostasis. Thus, by using a coding sequence specific for PTH or a PTH derivative, the device of the present invention is useful in controlling pathological and physiological conditions that are amenable to regulation by PTH, for example osteoporosis and calcium homeostasis. See, e.g., Lanske and Kronenberg, 1998, Crit. Rev. Eukaryot. Gene Expr. 8:297–320; Curtis et al., 1997, J. Endocrinol. 154:103–112; Jobert et al., 1996, Mol. Endocrinol. 10:1066–1076; U.S. Pat. Nos. 5,840,837; 5,814,607; 5,783,558; 5,420,242, which provide general background on PTH and which provide polynucleotide sequences for PTH and PTH derivatives useful for the device of the present invention.

5.3.1.1. Expression of Tyrosine Hydroxylase

Tyrosine hydroxylase ("TH") is an enzyme that catalyzes the conversion of tyrosine to dopa through a hydroxylation reaction. Dopa is a precursor of catecholamines which are neurotransmitters and the hydroxylation of tyrosine which results in dopa is the rate limiting step in the synthesis of catecholamins.

A lack of TH activity is observed in Parkinson's disease ("PD"), which is also characterized by the progressive loss of dopaminergic cells (see, e.g., Goetz et al., 1989, Patient Care 23:124–162) Transplantation of dopaminergic or genetically engineered cells expressing efficiently and permanently a functionally TH gene into the brain may provide a means of compensating for the loss of striatal dopamine in PD patients. Using this approach, several investigators have demonstrated partial restoration of abnormalities in rat models (see, e.g., Freed et al., 1992, New England Journal of Medicine 327:1549–1555; Lindvall et al., 1990, Science 247:574–577; Spencer et al., 1992, New England Journal of Medicine 327:1541–1548; Goetz et al., 1989, N. Engl. J. Med. 320:337–341).

Transplantation of cells to treat human diseases such as PD is limited because cells are quickly destroyed by the recipient's immune system. To overcome this limitation, attempts have been made to enclose hormone-secreting cells in a semipermeable membrane that would protect cells from immune attack, yet allow efflux of secretion products (see, e.g., Aebischer et al., 1991, Experimental Neurology 111:269–275; Winn et al., 1991, Experimental Neurology 113:322–329; Tresco et al., 1992, Cell Transplantation 1:225–264; Tseng et al., 1997, Journal of Neuroscience 17:325–333).

A polynucleotide specific for TH was used in the expression cassette of the device of the present invention, see Examples below. See, e.g., U.S. Pat. Nos. 5,300,436 and 5,212,082, which describe polynucleotides encoding various forms of TH and methods of processing and using those polynucleotides, all of which can be used in the device of the present invention.

As demonstrated in the Examples below, an exogenous polynucleotide that contains a TH specific cDNA sequence was amplified in mouse fibroblasts. It was further demonstrated that the exogenous polynucleotide was stably integrated and expressed in the cells when the cells were grown in the absence of selection. It was also shown that TH messenger RNA ("mRNA") was expressed at levels that correlated with the number of copies of the TH cDNA. Thus, the gene-amplification based expression system described herein is useful in providing high levels of TH activity as is desirable for the device of the present invention.

5.3.1.2. Melanoma Inhibitory Activity

Melanoma inhibitory activity ("MIA") is a protein capable of inhibiting the growth of melanoma cells. MIA is a protein of about 131 amino acids in its unprocessed form and about 107 amino acids after removal of a signal sequence. The mature MIA protein is secreted by cells. See, e.g., Bosserhoff et al., 1997, Development Dynamic 208:516–525; van Groningen et al., 1995, Cancer Research 55:6237–6243; Bogdahn et al., 1989, Cancer Research 49:5358–5363 and U.S. Pat. No. 5,770,366 for general background on MIA.

A MIA specific cDNA was incorporated in an exogenous polynucleotide useful for the device of the present invention and the resulting construct was introduced into mouse fibroblasts, as discussed below. As discussed below in the Examples and as shown in FIG. 4, the MIA cDNA was expressed at a high level when using the gene-amplification based expression system described herein.

5.3.2. Regulatory Sequences

The expression cassette used in the device of the present invention contains regulatory sequences designed to express the coding sequence or coding sequences, in case more than one coding sequence is used in the expression cassette. Typically, each coding sequence found in the expression cassette is operatively linked to at least two regulatory sequences, i.e., a promoter and a polyA sequence.

Any promoter that facilitates a sufficiently high rate of expression can be used in the expression cassette. The promoter may be constitutive or inducible. See, e.g., Resendez et al., 1988, Mol. Cell Biol. 8:4579–4584; Chang et al., 1987, Proc. Natl. Acad. Sci. USA 84:680–684, which describe inducible promoters. The choice of the promoter depends on what cell type is used in the device of the invention, on the species of animal in which the device is to be used, on the location (e.g., tissue or organ, for example the central nervous system) in the animal in which the device is to be used, the desired level of expression, the types and quantities of transcription factors available (i.e., in the cells of the device of the invention as a result of the cell type and the location in the recipient animal), etc. See, e.g., Gossen et al., 1995, Science 268:1766–1769; Gossen and Bujard, 1992, Proc. Natl. Acad. Sci. USA 89:5547–5551 and U.S. Pat. Nos. 5,851,984; 5,849,997; 5,827,687; 5,811,260; 5,789,215; 5,665,578; 5,512,483; 5,302,517; 4,959,313; 4,935,352, which describe promoter sequences useful for the device of the present invention.

Further examples of promoter sequences and elements are, without in any way limiting the present invention, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Omitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Another regulatory element used in the expression cassette is a polyA sequence (or polyA signal). The polyA sequence used should be capable of efficiently inducing polyadenylation of a transcript specific for the coding sequence to which the polyA sequence is operatively linked. See U.S. Pat. Nos. 5,861,290; 5,851,984; 5,840,525 and 5,627,033, which discuss polyA sequences.

In another embodiment, the expression cassette used in the device of the present invention contains an enhancer element, a 5' or 3' untranslated sequence (or region), an intron or a sequence that regulates RNA stability or a combination of more than one of these elements. Any sequence that falls into any of these categories can be used in the device of the present invention. See U.S. Pat. Nos. 5,861,290; 5,851,984; 5,840,525; 5,681,744 and 5,627,033, which discuss these regulatory elements. 5' untranslated sequence refers to the sequence of an mRNA molecule between the transcription initiation site and the translation initiation site. 3' untranslated sequence refers to the sequence of an mRNA molecule between the translation termination site and the polyA tail.

5.4. Selectable Markers

The cells used in the device of the present invention are transfected with the exogenous polynucleotide. The cells that take up the exogenous polynucleotide, typically through integration into their genome, are selected for following transfection. A selectable marker may be included in the exogenous polynucleotide that allows a cell that has the marker to be isolated from cells that do not have the marker. Whether a selectable marker is necessary to prepare the cells used in the device of the present invention, depends on the particular method by which the exogenous polynucleotide is introduced (i.e., transfected) into the cells. For example, if the exogenous polynucleotide is introduced into the cells via microinjection, a selectable marker is much less needed than if electroporation is used. For example, the marker may enable a cell to grow under selective conditions, i.e. conditions under which the cell could not grow if it did not have the marker (e.g., the neomycin resistance gene and the hypoxanthine phosphoribosyltransferase gene). A marker may also provide any other means by which to identify the cell which took up the exogenous polynucleotide (e.g., by staining the cells that took up the exogenous polynucleotide). See, e.g., U.S. Pat. Nos. 5,851,984 and 5,789,215, which describe selectable markers.

5.5. Cells

Any eukaryotic cell type can be used in the device of the present invention, for example fibroblasts, glial cells, keratinocytes, hepatocytes, ependymal cells, bone marrow cells, hippocampal cells, stem cells, embryonic stem cells, hematopoietic stem cells, olfactory mucosa cells, adrenal cells, leukocytes, lymphocytes, chromaffin cells, neurons, cells of the immune system, macrophages, Schwann cells, oligodendrocytes, astrocytes, germline cells, somatic cells, epithelial cells, endothelial cells, adrenal medulla cells, osteoblasts, osteoclasts, myoblasts, pancreatic cells (e.g., of the islets of Langerhans), or a mixtures of more than one of the above, etc. The cells used in the device of the present invention may be cells derived from a mammalian animal, a rodent, a farm animal, a mouse, a rat, a sheep, a dog, a cat, a cow, a pig, a bird, a fish, and most preferably a human. The cells should have the ability to proliferate when grown in culture so that the exogenous polynucleotide can amplify. Following transfection with the exogenous polynucleotide and selection for cells that took up the exogenous polynucleotide, the cells, in a preferred embodiment, should be able to establish a cell line that can be grown, stored, re-grown, etc., for extended periods of time. See, e.g., U.S. Pat. No. 5,814,618, which describes cells useful for the device of the present invention.

When cells are used that are very proliferative, it may be desirably to reduce the rate of proliferation of those cells before they are used in the device of the present invention. See, e.g., U.S. Pat. Nos. 5,853,717; 5,843,431; 5,840,576; 5,833,979 and 5,795,790, which describe methods to control proliferation of cells prior to encapsulation.

Cells used in the device of the present invention are grown, processed and prepared for encapsulation in any way known in the art. See, e.g., U.S. Pat. No. 5,650,148, which describes methods to prepare cells for encapsulation.

5.5.1. Transfection

The exogenous polynucleotide used in the device of the present invention is transfected into eukaryotic cells by any means known in the art. For example, electroporation, calciumphosphate coprecipitation, microinjection, lipofection, etc. can be used. See, e.g., U.S. Pat. Nos. 5,814,618 and 5,789,215, which describe transfection methods.

5.6. Capsules

The cells used in the device of the present invention are encapsulated before they are introduced into an animal. Encapsulation of the cells is designed to prevent an immune reaction to the cells in the host animal (e.g., a patient). For general background, see, e.g., Aebischer et al., 1994, Experimental Neurology 126:151–158; Tresco et al., 1992, Cell Transplantation 1:255–264; Aebischer et al., 1991, Experimental Neurology 111:269–275 and Winn et al., 1991, Experimental Neurology 113:322–329.

Depending on the particular design of the capsule used in the device of the invention, molecules up to a maximum size (i.e., in kilodalton weight ("kD")) will be able to move into and out of the capsule, i.e., molecular cut-off weight. The molecular cut-off weights useful for the device of the present invention is 1 kD, in another aspect it is 2 kD, in another aspect it is 5 kD, in another aspect it is 10 kD, in another aspect it is 25 kD, in another aspect it is 50 kD, in another aspect it is 100 kD and in yet another aspect it is 200 kD, or more. The material of the capsule should be such that it does not lead to any substantial adverse reactions in the host animal and it should allow the encapsulated cells to survive. In addition, the capsule should allow small molecules to move into and out of the interior of the capsule. In particular, if the cells inside the capsule generate a molecule that is designed to be a drug for the host animal, that molecule should be able to leave the capsule. Also, precursor molecules that are required by the cell to generate the drug molecule should be able to move into the capsule.

In a preferred embodiment, the capsule used in the device of the present invention makes it possible to use cells in the device that are derived from an animal different than the host animal. In another preferred embodiment, the cells are from a different species than the host (xenograft). In a further preferred embodiment, the capsule prevents a reaction of the immune system of the host to the cells and molecules from the cells so that, in a preferred aspect, no immunosuppressants are needed.

In another preferred embodiment, the capsule used in the device of the present invention has two layers, e.g., an inner sphere and an outer layer. In a preferred aspect, substantially all cells of the device are located in the inner layer (or sphere). In another aspect, a device of the present invention contains from about 40 to about 1,000 eukaryotic cells, more preferably from about 60 to about 500, more preferably from about 80 to about 250 and most preferably from about 80 to about 120 eukaryotic cells. However, capsules designed to house substantially larger numbers of cells can also be used in the device of the present invention, for example more than 1,000 cells, or more than 10,000 cells, or more than 50,000 cells, or more than 100,000 cells, or more than 500,000 cells, see, e.g., U.S. Pat. No. 5,800,828, which describes capsules that can house large numbers of cells.

Encapsulation methods and materials useful for the device of the present invention are described in, e.g., U.S. Pat. Nos. 5,853,385; 5,837,234; 5,834,001; 5,800,829; 5,800,828; 5,798,113; 5,762,959; 5,750,103; 5,676,943; 5,656,481; 5,653,975; 5,650,148; 5,639,275; 5,550,050 and 5,283,187.

5.7. Administration

The device of the present invention is transferred to a site in a host animal where the metabolic activity that is provided by the device is needed. In cases where the device cannot be transplanted to the most desirable location, it can be placed in a location that is sufficiently close so that the molecule that is provided by the device will be available at the desired site.

The device may be used in any organ or tissue of the recipient animal as the device is small and immunologically tolerable. Tissues in which the device of the invention may be located are connective tissue, muscle tissue, nerve tissue, epithelial tissue, etc. Organs in which the device of the invention may be located are the central nervous system, the spinal cord, the lumbar space, the peripheral nervous system, the pancreas, the liver, the kidneys, the lungs, the heart, the peritoneal cavity, the skeletal muscles, the organ muscles, the bones, cartilage, etc.

See, e.g., U.S. Pat. Nos. 5,800,828; 5,750,103; 5,650,148 and 5,550,050, which describe methods to transfer encapsulated cells into an animal.

5.8. Dosage

The device of the present invention will generally be used in an amount effective to achieve the intended purpose. For use to deliver a molecule lacking in a disease condition to an animal, e.g., a human (patient), the device of the present invention, in a pharmaceutically acceptable preparation thereof, is administered or applied in a therapeutically effective amount. By therapeutically effective amount is meant an amount effective to ameliorate or prevent the symptoms, or prolong the survival of, the animal being treated. Determination of a therapeutically effective amount is well within the capabilities of those skilled in the art.

A therapeutically effective dose can be estimated initially from in vitro assays using the molecule delivered by the device of the present invention. In an animal model, a dose can be formulated to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount may be adjusted individually to provide plasma levels of a therapeutically desirable molecule provided to the recipient animal by the device of the invention which are sufficient to maintain therapeutic effect.

The amount of the device of the invention administered will, of course, be dependent on the subject being treated, on the subject's weight, the severity of the affliction, the manner of administration and the judgment of the prescribing physician. Moreover, the specific design of the device of the invention will also determine what is a proper dosage.

The therapy may be repeated intermittently while symptoms are detectable or even when they are not detectable. The therapy may be provided alone or in combination with other drugs.

5.8.1. Toxicity

Preferably, a therapeutically effective dose of a device described herein will provide therapeutic benefit without causing substantial toxicity.

Toxicity of a device described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Devices which exhibit high therapeutic indices are preferred. The data obtained from these cell culture assays and animal studies can be used in formulating a dosage range that is not toxic for use in human. The dosage of a device described herein lies preferably within a range of concentrations that include the effective dose with little or no toxicity. The dosage may vary within this range depending upon the particular design of the device and the location in the recipient animal where the device is utilized. The exact formulation, route and location of administration and dosage can be chosen by the individual physician in view of the patient's condition. (See, e.g., Fingl et al., 1975, In: The Pharmacological Basis of Therapeutics, Ch. 1, p.1).

The invention having been described, the following examples are offered by way of illustration and not limitation.

6. EXAMPLES

6.1. Example 1

Encapsulated Cells Containing an Amplicied Expression Vector as a Drug Delivery Device

6.1.1. Materials and Methods
6.1.1.1. Plasmid Construction

A TH expression cassette was constructed by inserting the gene encoding for rat tyrosin hydroxylase between the mouse metallothionein-1 promoter (MMT) and the simian virus 40 polyadenylation signal (SV40 polyA). The TH cDNA was isolated as an 1.5 kb fragment from the initiation ATG codon to the KpnI site from pSPT-RTH (Grima et al., 1985, Proc. Natl. Acad. Sci. USA 82:617–621) and subcloned into the SmaI site of pBluescript KS(+) (Stratagene, Heidelberg, Germany), resulting in the plasmid pKS/rTH. To construct the TH expression cassette, the TH cDNA was excised from pKS/rTH by BamHI and EcoRV digestion and inserted into the SmaI and Bgl I site of pKSMMTneo (Meyer et al., 1993, Gene 129:263–268) yielding pKSM-MTrTH. For the final cloning step pKSMMTneo was digested by HindIII and XbaI for recovery of the TH expression cassette, the resulting 4300 bp fragment was integrated in the blunted Sal I site of pneotp-muPSl (Hemann et al., 1994, DNA and Cell Biology 13:437–445). The resulting TH expression plasmid, prTH, contains the three essential elements: (i) the TH expression cassette, (ii) the neomycin resistance cassette, and (iii) APSI as an amplification leading to high copy numbers in eucaryotic cells.

A MIA expression cassette was constructed by inserting a cDNA specific for MIA into the vector used above for TH. The MIA cDNA was obtained from Bogdahn et al., 1989, Cancer Research 49:5358–5363.

6.1.1.2. Cell Culture and DNA Transfection

L cells were cultured and transfected by the calcium phosphate precipitation procedure as described (Hemann et al., 1994, DNA and Cell Biology 13:437–445). Cells were exposed continuously to medium containing 600, 900 or 1200 μg/ml Geneticin (G418) (Gibco/BRL, Eggenstein, Germany). G418-resistant colonies were isolated and individually expanded to continuous cell lines.

6.1.1.3. Dot Blot Analysis

For dot blot analysis, $1\times10^6$ cells were suspended in 0.5 ml lysis buffer (10 mM EDTA, 10 mM Tris/HCl, 0.6% SDS). After adding 100 μg proteinase K, the cell lysate was incubated at 55° C. overnight and extracted twice with an equal volume of phenol, followed twice with phenol/chloroform and finally twice with chloroform. DNA was denatured by adding 0.1 volume of 3 M NaOH and incubated for 1 h at 68° C. After neutralizing with an equal volume of 2 M ammonium acetate pH 7.0, the DNA samples were applied to nylon membrane (Hybond-N+, DuPont, Cologne, Germany) using a dot blot device (BioRad, Munich, Germany). Hybridization was carried out as described by Church and Gilbert, 1984, Proc. Natl. Acad. Sci. USA 81:1991–1995. Copy numbers of the plasmid molecules were determined by volume integration using a PhosphorImager (Molecular Dynamics, Krefeld, Germany), with known amounts of vector DNA serving as references.

6.1.1.4. Northern Blot Analysis

Total cellular RNA was isolated using the TRIzol™ reagent (Gibco/BRL, Eggenstein-Leopoldshafen, Germany) according to the manufacturers instructions and RNA samples were electrophoresed in a 1.2% formaldehyde/agarose gel. The RNA was transferred to a nylon filter using 10×SSC as transfer buffer. After prehybridization in 6×SSC, 20 mM Tris/HCl, pH 7.5 and 10×Denhardt for 2–4 h at 65° C. with a $^{32}$P-labeled TH cDNA probe (specific activity: $1-2\times10^9$ cpm/μg DNA) in 6×SSC, 20 mM Tris/HCl, pH 7.5 5×Denhardt, 2 mM EDTA pH 8.0, 0.5% SDS and 0.2 mg/ml heat denatured salmon sperm DNA. Filters were washed in 0.1×SSC, 2 mM EDTA and 0.2% SDS once for 10 min at room temperature and twice for 30 min at 65° C. Subsequently, the membranes were exposed to X-ray films using an intensifying screen at −80° C. for one to several days.

6.1.1.5. Western Blot Analysis

Whole protein extracts from stable transfected cells were solubilized in SDS-sample buffer, boiled and separated in 8% SDS-polyacrylamide gel and transferred to nitrocellulose. Filters were probed with the monoclonal anti-TH antibody T-2928 (Sigma, Deisenhofen, Germany) and the anti-mouse IgG A-9044 (Sigma, Deisenhofen, Germany) as a peroxidase-coupled secondary antibody. The visualization was performed with the ECL system following the manufacturers recommendation (Amersham, Braunschweig, Germany).

6.1.1.6. Cytogenetic Analysis

Cytogenetic analysis was performed on metachromosome spreads as described (Zastrow et al., 1989, Nucl. Acids Res. 17:1867–1879).

6.1.1.7. L-Dopa Analysis

The content of L-dopa in L cell extracts and in the extracellular or extracapsular medium was determined essentially according to Tseng et al., 1997, J. Neuroscience 17:325–333.

6.2. Example 2

High Copy Numbers of Persisting Vector DNA in Transformed Mouse L Cells

Correlates with Expression of Rat TH

6.2.1. Stable Expression of TH Correlates With Gene Dosage

For overexpression of the TH gene in xenograft cells as a therapeutic approach for PD, a new vector was constructed as described in the Experimental protocols (FIG. 1). The plasmid, designated prTH, was used to transform mouse L fibroblasts. For copy number determination, transformed cells were analyzed by dot blot technique. As summarized in Table 1, the vast majority of clones bear much more than 10 copies of the transfected plasmid. Thus, transfection of the TH expression vector px leads to an efficient amplification of the vector DNA in most of the resulting transformed cell clones. The integrated vector DNA was stably maintained for more than 80 generations of nonselective growth without any significant reduction of copy numbers.

TABLE 1

Copy numbers of prTH plasmid in mouse L fibroblasts

| Group 1 Clones Copy Numbers ± SD* | Group 2 Clones Copy Numbers ± SD* | Group 3 Clones Copy Numbers ± SD* |
| --- | --- | --- |
| 17 ± 2.6 | 34 ± 8.1 | 75 ± 11.4 |
| 28 ± 5.1 | 45 ± 6.4 | 80 ± 6.8 |
| 15 ± 3.1 | 46 ± 14.6 | 105 ± 12.4 |
| 6 ± 4.0 | 56 ± 4.6 | 125 ± 9.7 |
| 14 ± 6.1 | 63 ± 2.9 | 128 ± 17.1 |
| 23 ± 1.1 | 44 ± 3.5 | 133 ± 8.2 |
| 26 ± 2.6 | 31 ± 3.2 | 140 ± 7.5 |
| 21 ± 8.5 | 64 ± 10.6 | |
| 18 ± 2.5 | 42 ± 2.1 | |
| | 47 ± 4.4 | |

Group 1 clones represent clones up to 30 transgen copies/cell.
Group 2 clones represent clones up to 70 transgen copies/cell.
Group 3 clones represent clones with more than 70 transgen copies/cell.
*Copy number determinations of 26 cell clones analyzed by dot blot technique as described in the Experimental protocols were carried out as triplicates and calculated per cell.
Standard deviations (SD) are indicated.

To determine whether copy numbers of prTH correlate with the expression rate, we analyzed the expression of rat TH mRNA and protein by Northern and Western blotting, respectively. Northern analyses of mRNA from transformed cell clones (FIG. 2A) showed that rat TH transcripts, which were detected in all clones examined, are expressed at high levels in all those cell lines bearing high numbers of the expression vector, but at much lower levels in low-copy-clones, indicating a direct correlation between copy numbers and the extent of TH expression. On the protein level, rat TH was detected by a specific monoclonal antibody which interacts with an N-terminal epitope and detects a 60 kD protein. FIG. 2B demonstrates that rate TH protein can be detected at high amounts in all those cell lines bearing high numbers of px molecules, whereas the protein level is significantly lower in low-copy clones. Thus, TH expression both on the transcriptional and translational level correlates positively with copy numbers of the expression plasmid, reflecting a positive gene dosage effect.

6.2.2. In Situ Hybridization of TH Plasmid DNA

To determine whether the plasmid DNA persists in transformed mouse cells episomally or integrated into the genome, metaphase chromosomes were prepared and hybridized in situ to plasmid probes labeled with biotin. The biotin-labeled nucleotides were detected by binding peroxidase-conjugated streptavidin, and then developing with diaminobenzidine (DAB). The precipitate that formed at the site of hybridization was visualized by reflection-contrast microscopy. FIGS. 3a–d shows representative photographs of two different chromosome spreads in two different magnifications. The signals obtained with biotin-labeled plasmid probes in each case were visible as dots on a single chromosome. This hybridization patten indicates the amplification and integration of the transfected plasmid DNA into the host genome forming an extended homogeneously staining region (HSR).

6.3. Example 3

High Copy Numbers of Persisting Vector DNA in Transformed Mouse L Cells

Correlates with Expression of Rat MIA 6.3.1. Expression of MIA Correlates With Gene Dosage A vector with an expression cassette for MIA and APSI was constructed as for TH and transfected into mouse L fibroblasts. The number of copies of the MIA cassette per cell in 15 clones was determined at more than 30 copies per cell in 80% of the clones and more than 100 copies per cell in 45% of the clones. This demonstrates that the APS1 sequence amplifies the MIA expression cassette in-mouse L cells.

FIG. 4 further demonstrates that the level of MIA specific mRNA in the L cells correlated with the number of copies of the MIA cassette.

6.4. Example 4

Expression of Enkephalins and Enkephalin Precursors and Enzymes that Process enkephalin Precursors 6.4.1. Endiphalin Production Using the Device of the Invention In the following example, enkephalins are produced using the device of the present invention. Enkephalins are neurohormone peptides that are synthesized in vivo as precursor polypeptides called preproenkephalin and proenkephalin which are processed to yield the enkephalin peptides (see, e.g., Kang et al., 1998, Brain Research 792:133–135; Liu et al., 1996, Journal of Neurochemistry 67:1457–1462). The processing of the preproenkephalin and proenkephalin polypeptide is carried out by peptidases, for example enkephalinase. See, e.g., U.S. Pat. Nos. 5,780,025 and 5,403,585, which describe enkephalinase and methods for its use.

In this example, the device of the present invention includes a cDNA specific for a precursor polypeptide of enkephalins. See, e.g., Kang et al., 1998, Brain Research 792:133–135; Liu et al., 1996, Journal of Neurochemistry 67:1457–1462, which describe enkephalin specific polynucleotides. The cells used in this aspect are of from the cell line AtT-20/D 16v-F2 (ATCC No. CRL-1795) which is capable of processing the enkephalin precursor that is encoded by the cDNA of the expression cassette. The device described in this example generates enkephalins at high amounts over extended periods of time. When used to express an enkephalin in a patient, the device of the invention is located in the lumbar vertebrae area.

6.5. Example 5

Expression of Tryptophan Hydroxylase 6.5.1. Serotonin Production Using the Device of the Invention In the following example, the device of the present invention is used for the generation of serotonin, i.e., 5-hydroxytryptophan. The rate limiting step in the synthesis of serotonin is the hydroxylation of tryptophan by the enzyme tryptophan hydroxylase (see, e.g., Wang et al., 1998, Journal of Neurochemistry 71 :1769–1772; Tipper et al., 1994, Arch. Biochem. Biophys. 315:445–453; Kim et al., 1991, Brain Res. Mol. Brain Res. 9:277–283; Hamon et al., 1981, Journal of Physiology 77:269–279). Serotonin is generated using the device of the present invention by incorporating a polynucleotide sequence specific for tryptophan hydroxylase into the expression cassette of the exogenous polynucleotide.

6.6. Example 6

Expression of Insulin, Glucokinase and Glut-2 Glutose Transporter Protein 6.6.1. Insulin Production Glucose Sensitive Insulin Expression In the following example, a polynucleotide sequence specific for insulin or an insulin precursor is used in the expression cassette of the device of the invention. See, e.g., U.S. Pat. Nos. 5,792,656 and 4,914,026, which discuss polynucleotides specific for insulin. The insulin specific polynucleotide is operatively linked to a promoter that is responsive to induction by elevated concentrations of glucose. See, e.g., Marie et al., 1993, J. Biol. Chem. 268:23881–23890, which describes a glucose inducible promoter. The device of the invention, if designed with a glucose responsive promoter element and an insulin (or insulin precursor) specific polynucleotide, is capable of generating insulin in the recipient animal when the glucose levels in that animal are elevated. Thus, the device generates insulin in a glucose dependent manner, as is observed in the islets of Langerhans in the pancreas.

6.6.2. Increase Insulin Production Through Expression of Glucose Sensing Molecules In the following example, an exogenous polynucleotide that provides a glucose sensing activity is used in the device of the invention. Glucokinase and GLUT-2 are part of the glucose sensing mechanism in cells. In this example, a glucokinase polynucleotide, a GLUT-2 polynucleotide, or both are expressed in the exogenous polynucleotide of the device of the present invention. The cells used in this aspect of the invention are capable of expressing and processing insulin. The expression cassette does not express glucokinase if the cells express glucokinase. See, e.g., U.S. Pat. Nos. 5,792,656 and 5,747,325, which describe cells and polynucleotides useful for this aspect of the present invention.

6.7. Example 7

Expression of PTH and PTH Precursor Proteins

In the following example, a polynucleotide specific for a PTH precursor is used in the expression cassette of the device of the invention. The PTH cDNA clone used in this example is obtained from IMAGE Consortium, LLNL through Max Planck Institute, Berlin, Germany, i.e., clone DbEST No. 564041 (also named IMAGp998D12740). PTH is a peptide hormone involved in the regulation of calcium metabolism. PTH is useful in controlling disease conditions, for example osteoporosis. See, e.g., Lanske and Kronenberg, 1998, Crit. Rev. Eukaryot. Gene Expr. 8:297–320; Curtis et al., 1997, J. Endocrinol. 154:103–112; Jobert et al., 1996, Mol. Endocrinol. 10:1066–1076; U.S. Pat. Nos. 5,840,837; 5,814,607; 5,783,558; 5,420,242, which provide general background on PTH and which provide polynucleotide sequences for PTH and PTH derivatives useful for the device of the present invention. PTH is used to regulate calcium homeostasis. Thus, a promoter element that is responsive to changes in calcium concentrations in the cell is operatively linked to the PTH specific polynucleotide. See, e.g., Resendezlet al., 1988, Mol. Cell Biol. 8:4579–4584; Chang et al., 1987, Proc. Natl. Acad. Sci. USA 84:680–684, which describe calcium responsive promoters.

The present invention is not to be limited in scope by the exemplified embodiments which are intended as illustrations of single aspects of the invention, and any clones, nucleotide or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

What is claimed is:

1. An encapsulated population of cells comprising
    (a) a eukaryotic cell;
    (b) an exogenous polynucleotide comprising an expression cassette and an amplification-promoting sequence, said eukaryotic cell comprising said polynucleotide, wherein said expression cassette is stably expressed and comprises a nucleic acid encoding an insulin, an insulin precursor polypeptide, a serotonin, a neurotropic factor, a neurotrophic factor, a tyrosine hydroxylase, a tryptophan hydroxylase, an enkephalin, an enkephalin precursor polypeptide, an enkephalinase, a melanoma inhibitory activity and parathyroid hormone and wherein said amplification-promoting sequence comprises a polynucleotide that is capable of hybridizing under highly stringent conditions to a polynucleotide that is complementary to SEQ ID NO:1 or SEQ ID NO:2; and
    (c) a capsule, said eukaryotic cell being located in the interior of said capsule.

2. The encapsulated population of cells of claim 1, wherein the amplification-promoting sequence is a polynucleotide comprising the sequence of SEQ ID NO:1.

3. The encapsulated population of cells of claim 1, wherein the amplification-promoting sequence is a polynucleotide comprising the sequence of SEQ ID NO:2.

4. The encapsulated population of cells of claim 1, wherein the amplification-promoting sequence comprises a polynucleotide that is capable of hybridizing under highly stringent conditions to a polynucleotide that is complementary to SEQ ID NO:1.

5. The encapsulated population of cells of claim 1, wherein the amplification-promoting sequence comprises a polynucleotide that is capable of hybridizing under highly stringent conditions to a polynucleotide that is complementary to SEQ ID NO:2.

6. The encapsulated population of cells of claim 1, wherein the expression cassette comprises a coding polynucleotide sequence and a regulatory polynucleotide sequence.

7. The encapsulated population of cells of claim 6, wherein the regulatory polynucleotide sequence comprises a promoter and a polyA signal.

8. The encapsulated population of cells of claim 7, wherein the regulatory polynucleotide sequence further comprises a regulatory polynucleotide sequence selected from the group consisting of an intron, an enhancer, a 5' untranslated region, a 3' untranslated region and an RNA stability regulating sequence.

9. The encapsulated population of cells of claim 7, wherein the promoter is inducible.

10. The encapsulated population of cells of claim 7, wherein the promoter is constitutive.

11. The encapsulated population of cells of claim 1, wherein the exogenous polynucleotide further comprises a selectable marker.

12. The encapsulated population of cells of claim 11, wherein the selectable marker confers the ability to grow under selective growth conditions.

13. The encapsulated population of cells of claim 12, wherein the selectable marker is selected from the group consisting of the neomycin resistance gene and the hypoxanthine phosphoribosyltransferase gene.

14. The encapsulated population of cells of claim 1, wherein the capsule is double layered.

15. The encapsulated population of cells of claim 1, wherein the capsule comprises an inner core and an outer shell.

16. The encapsulated population of cells of claim 15, wherein the eukaryotic cell is located in the inner core.

17. The encapsulated population of cells of claim 15, wherein the capsule was made using alginate.

18. The encapsulated population of cells of claim 17, wherein substantially all of from about 40 to about 1000 eukaryotic cells, into which said exogenous polynucleotide has been introduced, are located in the inner core.

19. The encapsulated population of cells of claim 17, wherein substantially all of from about 60 to about 500 eukaryotic cells, into which said exogenous polynucleotide has been introduced, are located in the inner core.

20. The encapsulated population of cells of claim 17, wherein substantially all of from about 80 to about 250 eukaryotic cells, into which said exogenous polynucleotide has been introduced, are located in the inner core.

21. The encapsulated population of cells of claim 17, wherein substantially all of from about 80 to about 120 eukaryotic cells, into which said exogenous polynucleotide has been introduced, are located in the inner core.

* * * * *

SEQUENCE LISTING

<160> NUMBER OF SEQ ID NOS: 2

<210> SEQ ID NO 1
<211> LENGTH: 370
<212> TYPE: DNA
<213> ORGANISM: Mus musculus

<400> SEQUENCE: 1

```
cttagtcttc aagtctgagt tactggaaag gagttccaag aagactggtt atatttttca      60
tttattattg cattttaatt aaaatttaat ttcaccaaaa gaatttagac tgacaaattc     120
agagtctgcc gtttaaaagc ataaggaaaa agtaggagaa aaacgtgagg ctgtctgtgg     180
atggtcgagg tcgctttagg gagcctcgtc accattctgc acttgcaaac cgggccacta     240
gaacccggtg aagggagaaa ccaaagcgac ctggaaacaa taggtcacat gaaggccagc     300
cacctccatc ttgttgtgcg ggagttcagt tagcagacaa gatggctgcc atgcacatgt     360
tgtctttcag                                                           370
```

<210> SEQ ID NO 2
<211> LENGTH: 423
<212> TYPE: DNA
<213> ORGANISM: Mus musculus

```
<400> SEQUENCE: 2
atcatgaagg cacattggat tttatgacag agtctgtgtg tgtgtgtgtg tataatattt      60
ctgctatgat tgcagttact tgccatctcg tgggcttatg tttgatttct gtagtttttt    120
aaaattcttt aaaattttta ttttatattt ttttagttta gtttagttta atttagttta    180
gttttcaaga cagggtttct ctgtatagcc ctgactgtcc tggaactcac tttgcagacc    240
aggctggcct caaactcaga aatcctccca tctctgcctg aagagagctg ggattaaaga    300
catgcgccat cactcccggc tattttaaa tttttaaatt atatttattt aatttatttt     360 tttgttttt tcaagatgtg gtttctctgt gtaaactctg gctgacctgg aactcactgt     420
gta                                                                  423
```